United States Patent
Ono et al.

(10) Patent No.: US 11,330,774 B2
(45) Date of Patent: May 17, 2022

(54) HYDROPONIC CULTURE METHOD FOR PLANT IN HIGH SALINITY ENVIRONMENT

(71) Applicant: SEKISUI CHEMICAL CO., LTD., Osaka (JP)

(72) Inventors: Seigo Ono, Tsukuba (JP); Toshimasa Takeuchi, Tsukuba (JP); Setsuo Nakajima, Tokyo (JP); Koichiro Iwasa, Tokyo (JP); Makoto Fujigami, Fujisawa (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 955 days.

(21) Appl. No.: 15/774,357

(22) PCT Filed: Dec. 14, 2016

(86) PCT No.: PCT/JP2016/087261
§ 371 (c)(1),
(2) Date: May 8, 2018

(87) PCT Pub. No.: WO2017/110626
PCT Pub. Date: Jun. 29, 2017

(65) Prior Publication Data
US 2020/0245576 A1    Aug. 6, 2020

(30) Foreign Application Priority Data
Dec. 24, 2015 (JP) ............... JP2015-252456

(51) Int. Cl.
| | | |
|---|---|---|
| A01H 1/04 | (2006.01) | |
| A01G 31/00 | (2018.01) | |
| A01G 31/02 | (2006.01) | |
| A01N 59/08 | (2006.01) | |
| C12N 1/20 | (2006.01) | |
| A01N 63/25 | (2020.01) | |

(52) U.S. Cl.
CPC ............ *A01G 31/00* (2013.01); *A01G 31/02* (2013.01); *A01N 59/08* (2013.01); *A01N 63/25* (2020.01); *C12N 1/20* (2013.01)

(58) Field of Classification Search
CPC .......... A01G 31/00; A01G 31/02; C12N 1/20
USPC ..................................... 504/116.1
See application file for complete search history.

(56) References Cited

FOREIGN PATENT DOCUMENTS

| CN | 102187773 | 9/2011 |
|---|---|---|
| JP | 2010-209000 | 9/2010 |
| JP | 5013326 | 8/2012 |
| JP | 2013-75881 | 4/2013 |
| JP | 2015-57950 | 3/2015 |

OTHER PUBLICATIONS

Lee et al. Agroforest Syst. 80: 333-340, 2010.*
Nautiyal et al. Plant Physiology and Biochemistry 66: 1-9, 2013.*
Kratky. Proc. IS on Soilless Culture and Hydroponics. Acta Hort. 843, ISHS. pp. 65-71. 2009.*
Office Action dated May 7, 2020 in corresponding Singaporean Patent Application No. 11201803868R.
Lee et al., "Beneficial bacteria and fungi in hydroponic systems: Types and characteristics of hydroponic food production methods", Scientia Horticulturae, 2015, vol. 195, pp. 206-215.

* cited by examiner

*Primary Examiner* — Keith O. Robinson
(74) *Attorney, Agent, or Firm* — Wenderoth, Lind & Ponack, L.L.P.

(57) ABSTRACT

The present invention provides a plant cultivation method, which enables plant cultivation under high salinity environment for a long time. A method for hydroponic plant cultivation under high salinity environment, comprising a cultivation step of hydroponically growing a plant with a cultivation solution having a sodium chloride concentration of 1% by mass or more, during which a salt resistance imparting treatment is performed at least once by bringing a salt tolerance imparting agent into contact with at least a part of a root of the plant, thereby maintaining salt tolerance of the plant.

9 Claims, No Drawings

HYDROPONIC CULTURE METHOD FOR PLANT IN HIGH SALINITY ENVIRONMENT

TECHNICAL FIELD

The present invention relates to a method for hydroponically growing a plant stably for a long time with a cultivation solution having a sodium chloride concentration of 1% by mass or more.

BACKGROUND ART

In recent years, a need for a large amount of agricultural water has arisen due to the increase in food production accompanying the population increase in various countries around the world, and water shortage has become a serious problem. The water resource which is the most abundant on the earth is sea water, and if seawater can be used as agricultural water, this problem can be solved. However, most plants cannot be grown under the high salinity condition due to water absorption inhibition by osmotic pressure and inhibition of intracellular enzymes by sodium ions. If plants with low salt tolerance can be improved to have enhanced tolerance against salt up to salinity of the seawater level, such improvement is expected to enable cultivation of the plants using seawater.

One example of method for enhancing the salt tolerance of plants is a method of introducing a gene related to a salt tolerance mechanism by gene recombination technology. For example, there are halophilous plants that have acquired resistance to osmotic pressure by accumulating osmolytes (proline or betaine) in their plant cells. It has been reported that a genetically-modified plant into which a gene inducing osmolyte accumulation has been introduced acquires salt tolerance. Further, it is known that an activation of SOS1 gene promotes extracellular discharge of sodium ions, and researches have been made on genetically-modified plants into which this gene has been introduced.

As regards a method for enhancing the salt tolerance of plants without using gene recombination technology, studies have been made on a method in which plants are administered with drugs or microorganisms which have an effect of imparting salt tolerance to plants. As a drug effective for imparting salt tolerance, for example, pyrroloquinoline quinone (see, for example, Patent Document 1) and strigolactones which are plant hormones and the like are known. Further, as a microorganism effective for imparting salt tolerance, for example, *Paenibacillus fukuinensis* is known (see, for example, Patent Document 2).

PRIOR ART REFERENCES

Patent Document

Patent Document 1: Japanese Patent Granted Publication No. 5013326
Patent Document 2: Japanese Unexamined Patent Application Publication No. 2013-75881

SUMMARY OF THE INVENTION

Problems to be Solved by the Invention

Since the mechanism of influence of salt is very complicated, sufficient salt tolerance cannot be acquired simply by introducing one species of gene. In fact, most of the genetically modified plants to which genes involved in the mechanism related to salt tolerance have been introduced are confirmed to have tolerance against up to about 100 mM of sodium chloride, which is not sufficient to grow the plants with seawater instead of fresh water. Further, genetically modified plants have a problem related to safety concerns etc.

In some cases, a drug effective for imparting salt tolerance itself inflicts stress on plants. Therefore, generally, such a drug can be used for plants only for a limited period of time. In addition, culturing microorganisms is often costly and laborious, and it is often difficult from an economic point of view to use microorganisms over the whole period for glowing plants. Furthermore, the salt tolerance imparted by chemicals and microorganisms does not last permanently; therefore, it is difficult to glow plants under high salinity environment for a long time by performing the salt tolerance imparting treatment only once.

It is an object of the present invention to provide a plant cultivation method, which enables plant cultivation under high salinity environment for a long time.

Means to Solve the Problems

The method for hydroponically growing a plant under high salt concentration environment according to the present invention are as described below in [1] through [9].

[1] A method for hydroponic plant cultivation under high salinity environment, comprising a cultivation step of hydroponically growing a plant with a cultivation solution having a sodium chloride concentration of 1% by mass or more, during which a salt resistance imparting treatment is performed at least once by bringing a salt tolerance imparting agent into contact with at least a part of a root of the plant, thereby maintaining salt tolerance of the plant.

[2] The method according to [1] above, wherein the salt tolerance imparting treatment is a treatment of soaking at least a part of the root of the plant into a treatment solution which contains the salt tolerance imparting agent, and has a sodium chloride concentration of 1% by mass or more.

[3] The method according to [2] above, wherein at least a part of the root of the plant is held in the treatment solution for 1 hour or more.

[4] The method according to [2] or [3] above, wherein the cultivation solution further contains magnesium chloride in an amount of 0.5% by mass or less.

[5] The method according to [1] to [4] above, wherein the salt tolerance imparting agent comprises at least one microorganism.

[6] The method according to any one of [1] to [4] above, wherein the salt tolerance imparting agent comprises at least one microorganism that imparts the salt tolerance to the plant by adhering to the root, and
the concentration of the microorganism in the treatment solution is $10^3$ CFU/mL or more.

[7] The method according to any one of [1] to [6] above, which is performed using a hydroponic cultivation apparatus comprising:
a cultivation tank for storing the cultivation solution;
a cultivation pot for accommodating the plant; and
a float having one or more through-holes for fitting the cultivation pot, which is floated on the surface of the cultivation solution.

[8] The method according to [7], wherein the salt tolerance imparting treatment comprises:
a water level adjustment step of adjusting an amount of water in the cultivation tank to be smaller than that in the cultivation step;

a mixing step of mixing the salt tolerance imparting agent into the cultivation solution in the cultivation tank after the water level adjustment step; and a treatment step of cultivating the plant for at least one hour after the mixing step, while allowing the root of the plant to be in contact with the salt tolerance imparting agent.

[8] The method according to 7, wherein the salt tolerance imparting treatment comprises:

a transfer step of allowing the float with the cultivation pot accommodating the plant to float on a surface of the cultivation solution, the cultivation pot being fitted into the through-hole of the float; and a treatment step of cultivating the plant for at least one hour after the transfer step, while allowing the root of the plant to be in contact with the salt tolerance imparting agent.

Effect of the Invention

According to the method of the present invention for hydroponic plant cultivation under high salinity environment, a plant originally having low salt tolerance can be hydroponically cultivated stably for a long time with a cultivation solution having a sodium chloride concentration of 1% by mass or more while using a drug or a microorganism having a salt resistance imparting effect.

DESCRIPTION OF THE EMBODIMENTS

The method for hydroponic cultivation of a plant under high salinity environment according to the present invention (hereinafter, also referred to as "hydroponic method of the present invention") is a method for growing a plant originally having low salt tolerance by treating the plant with the salt tolerance imparting agent, thereby enabling the plant to be grown under very high salinity environment, i.e., a sodium chloride concentration of 1% by mass or more. The effect of the salt tolerance imparting agent that improves a posteriori the salt tolerance of plants does not last permanently. Therefore, for glowing a plant under high salinity environment for a long time, treating the plant with the salt tolerance imparting agent only once is not enough, and the treatment need to be performed additionally once or more during cultivation of the plant even after the plant has acquired the salt tolerance. In this situation, the hydroponic method of the present invention comprises a cultivation step of hydroponically growing a plant with a cultivation solution having a sodium chloride concentration of 1% by mass or more, during which a salt resistance imparting treatment is performed at least once by bringing a salt tolerance imparting agent into contact with at least a part of a root of the plant, thereby maintaining salt tolerance of the plant. By performing the salt resistance imparting treatment during the cultivation step, the salt tolerance of the plant can be maintained for a long period of time. Therefore, the hydroponic method of the present invention, when, for example, applied to cultivation of agricultural crops, enables the plant cultivation to be continued until harvesting under high salinity environment.

In the present invention, the sodium chloride concentration of the cultivation solution in the cultivation step is not limited as long as the sodium chloride concentration is 1% by mass or more, and may be appropriately adjusted in accordance with the salt tolerance of the plant to be cultivated. The sodium chloride concentration of the cultivation solution used in the present invention may be 1 to 4% by mass, preferably 1.5 to 3.8% by mass, and more preferably 2 to 3.5% by mass.

The cultivation solution used in the present invention may contain magnesium chloride in addition to sodium chloride, where the amount of magnesium chloride contained may be 0.5% by mass or less, or may be 0.1 to 0.5% by mass.

In addition to sodium chloride and magnesium chloride, it is preferable that the cultivation solution used in the present invention contains various nutrient components which are necessary for the growth of the plant. The nutrient components can be appropriately adjusted according to the type of the plant to be cultivated. Especially, it is preferable that the cultivation solution contains elements necessary for plant growth in the form of salts. Examples of such elements include nitrogen, phosphorus, potassium, calcium, magnesium, sulfur, iron, manganese, copper, molybdenum, and boron. The cultivation solution may further contain elements such as aluminum and silicon in the form of salts thereof, depending on the type of the plant. Further, the composition of the cultivation solution may be varied according to the growth stage of the plant.

The cultivation solution to be used in the present invention may be, for example, a solution prepared by supplementing deficient salt such as sodium chloride to commercially available liquid fertilizer or a solution obtained by diluting commercially available concentrated liquid fertilizer with sea water instead of water. Further, the cultivation solution may also be a solution obtained by appropriately adding a deficient salt such as salt of phosphorus to seawater.

In the present invention, the hydroponic cultivation in the cultivation step may be performed by a general hydroponic cultivation method, except that the sodium chloride concentration of the cultivation solution is set to 1% by mass or more. The cultivation step may be performed by a deep flow technique in which a relatively large amount of the cultivation solution is stored in the cultivation tank, or a nutrient film technique in which a culture solution is allowed to flow down little by little on a flat surface having a gentle slope.

In the deep flow technique, the replacement of the cultivation solution in the cultivation tank may be carried out by a circulation method in which the cultivation solution used is circulated, or a non-circulation method in which the cultivation solution used for a certain period of time in the cultivation tank is drained. In case of the circulation method, the cultivation solution prepared in a cultivation solution preparation tank is charged into the cultivation tank by a pump or the like, and is collected back to the cultivation solution preparation tank from the cultivation tank, and the nutrient component or the like is prepared.

For example, the deep flow technique can be carried out by using a hydroponic cultivation apparatus having: a cultivation tank for storing the cultivation solution; a cultivation pot for accommodating the plant; and a float which has one or more through-holes for fitting the cultivation pot, and is to be floated on the surface of the cultivation solution. The cultivation pot may be detachably fitted into the through-hole of the float, or may be fixed undetachably to the through-hole of the float. Alternatively, the float and the cultivation pot may be integrally formed. The cultivation tank may be installed indoors, or may be installed outdoors.

In the case of a circulation type hydroponic cultivation apparatus, the cultivation tank includes a water supply hole for injecting the cultivation solution, and a drainage hole for draining the cultivation solution. In the case of a non-circulation type hydroponic cultivation apparatus, the cultivation tank may include both of the water supply hole and the drainage hole, or may include a water supply/drainage hole used for both of the water supply and the drainage. The water supply and drainage of the cultivation solution to and from the cultivation tank are controlled by a pump and a valve.

The cultivation pot is a container that has openings at least on an upper surface and a lower surface, and is capable of retaining the supporting carrier. In general, the cultivation pot formed of a resin material such as polyethylene, polypropylene, or polyvinylidene chloride is used. By allowing the plant to grow such that a stem or a leaf grows upward from the supporting carrier, and the root grows downward into the supporting carrier, the plant can be grown in a state of being supported by the supporting carrier. The supporting carrier is not particularly limited as long as it has such a porosity that allows the roots of the plant penetrate the supporting carrier while being held in a cultivation pot, and may be, for example, a gel material, a fibrous material, or a granular or gravel-shaped material. Examples of the gel material include polysaccharide polymers such as agar, agarose, gellan gum, and alginic acid; and water absorptive resins such as acrylic resin. Examples of the fibrous material include non-woven fabric, cotton, paper, rock wool, and glass wool. Examples of the granular or gravel-shaped material include a wood chip, a bark, pumice, vermiculite, and sand.

The float is formed of a material that floats on the surface of the cultivation solution in a state where the cultivation pot being used for cultivating the plant is fitted into the through-hole. As such a material, for example, a foamed resin such as polystyrene foam or polypropylene foam is used. By fitting the cultivation pot into the float, the cultivation pot can be always positioned on the surface of the cultivation solution, regardless of whether the amount of the cultivation solution is large or small, and even if the amount of the cultivation solution is small, the root of the plant can be allowed to contact constantly with the cultivation solution.

The float to be floated in the cultivation tank may be one sheet, or two or more sheets. When the cultivation tank is installed outdoors, it is preferable that the float is installed to cover most of the surface of the cultivation solution, in order to prevent evaporation of the cultivation solution from the surface thereof.

In the deep flow technique, it is preferable that the hydroponic cultivation apparatus used includes oxygen supply means for keeping the dissolved oxygen content of the cultivation solution at a predetermined level or higher. As the oxygen supply means, for example, an air pump or an air sucker can be used. By installing the air pump in the cultivation tank, air including oxygen can be directly supplied to the cultivation solution in the cultivation tank. When the air sucker is used, the cultivation solution can be charged into the cultivation tank after the cultivation solution is mixed with air by passing the cultivation solution through the air sucker or the like in advance.

The pH suitable for the hydroponic cultivation varies depending on the kind of the plant, and is generally approximately 5.5 to 6.5, but the pH of the cultivation solution tends to increase as the cultivation period extends longer. Therefore, in order to stably perform the hydroponic cultivation for a long period of time, it is preferable that the hydroponic cultivation apparatus used includes pH control means for measuring the pH of the cultivation solution periodically, and dosing an acid material in order to adjust the pH within a predetermined range as necessary. As the acid material used for the pH adjustment, for example, hydrochloric acid, sulfuric acid, or nitric acid can be used.

In the hydroponic cultivation method of the present invention, the salt tolerance imparting treatment can be performed by soaking at least a part of the root of the plant into a treatment solution containing the salt tolerance imparting agent and having a sodium chloride concentration of 1% by mass or more. The treatment solution may be a solution obtained by mixing the salt tolerance imparting agent with the cultivation solution, and may have a composition of salts different from that of the cultivation solution.

The salt tolerance imparting agent used in the present invention may be a drug, a microorganism, or a culture supernatant of the microorganism. Examples of the drug include pyrroloquinoline quinone (see Patent Document 1) and strigolactone. Examples of the microorganism include *Paenibacillus fukuinensis* (see Patent Document 2). The salt tolerance imparting agent may be formed of one kind of microorganism, or a mixture of two or more kinds of microorganisms.

The concentration of the salt tolerance imparting agent in the treatment solution can be appropriately adjusted in consideration of the kind of the salt tolerance imparting agent, the kind of the plant, the growth stage or the like. When the concentration of the salt tolerance imparting agent in the treatment solution is too low, the salt tolerance imparting agent is less likely to get in contact with the root of the plant in the treatment solution, which may result in insufficient salt tolerance imparting effect. On the other hand, depending on the kind of the salt tolerance imparting agent, the growth of the plant may be adversely affected by excessive intake of the salt tolerance imparting agent. In view of this, an appropriate concentration of the salt tolerance imparting agent in the treatment solution for obtaining sufficient salt tolerance imparting effect can be determined empirically. For example, when the salt tolerance imparting agent is the microorganism, the concentration of the microorganism in the treatment solution may be set to be 103 CFU/mL or more, whereby sufficient salt tolerance imparting effect can be obtained.

The time period for performing the salt tolerance imparting treatment time once, that is, the time for holding at least a part of the root of the plant to be soaked in the treatment solution, can be appropriately adjusted in consideration of the kind of the plant or the kind of the salt tolerance imparting agent to be used. For example, such time period for the salt tolerance imparting treatment is preferably 1 hour or more, more preferably 18 hours or more, still preferably one day or more, and further more preferably one day to seven days. Cultivating the plant for 1 hour or more with the root thereof being soaked in the treatment solution ensures sufficient chance for the salt tolerance imparting agent in the treatment solution to contact the root of the plant, whereby the salt tolerance can be imparted more easily.

The salt tolerance imparting treatment may be performed in situ in the cultivation tank where the plant has been grown, or the plant that has been grown in the cultivation tank may be transferred to a treatment tank storing the treatment solution so as to perform the salt tolerance imparting step in the treatment tank.

When the salt tolerance imparting treatment is performed in the cultivation tank, the salt tolerance imparting agent may be directly charged into the cultivation solution in the cultivation tank, or the treatment solution prepared in advance in another tank may be supplied to the cultivation tank from which the cultivation solution has been drained. When the salt resistance imparting agent is charged into the circulating cultivation solution in the form of supplementary fertilizer, a concentration gradient of the salt resistance imparting agent occurs in the cultivation solution, which may result in insufficient salt resistance imparting effect. In order to prevent the occurrence of such a concentration gradient of the salt tolerance imparting agent, it is preferable that the treatment solution is contacted with the root of the plant while suppressing the amount of the water supply and drainage or without the water supply and drainage. However, when the amount of the water supply and drainage is small or the water supply and drainage is not performed, the stagnation may occur in the cultivation tank, causing adverse effect on the plant itself. Therefore, it is preferable that the treatment solution is suitably stirred by the bubbling treatment with an air pump.

When the salt tolerance imparting treatment is performed in the treatment tank, the cultivation pot with the plant may be detached from the float of the cultivation tank, and may be fitted into the through-hole of the float floating on the surface of the cultivation solution stored in the treatment tank, or the float into which the cultivation pot is embedded may be transferred from the cultivation tank to be floated on the surface of the cultivation solution in the treatment tank. Transfer means for transferring the cultivation pot or the float to the treatment tank from the cultivation tank is not particularly limited, and for example, the transfer may be performed by means of a water current, or a conveyor. When a plurality of cultivation pots are installed per treatment tank, it is preferable that a bubbling treatment is performed by an air pump, in order to prevent stagnation of the treatment solution, and oxygen deficiency.

The larger the amount of the treatment solution used in the salt tolerance imparting treatment, the larger the amount of the salt tolerance imparting agent needed. Therefore, by reducing the amount of the treatment solution to an amount that is necessary and sufficient to allow the root of the plant grown from the bottom surface of the cultivation pot to contact the treatment solution, the amount of the salt tolerance imparting agent required for performing the salt tolerance imparting treatment once can be suppressed. When the salt tolerance imparting treatment is performed in the treatment tank, the amount of the treatment solution can be suppressed by using a treatment tank which is smaller than the cultivation tank. However, when the amount of the treatment solution is too small, it may become impossible to allow a sufficient amount of the salt tolerance imparting agent to contact the root of the plant. Therefore, when a plate into which one cultivation pot is fitted is installed per treatment tank, the amount of the treatment solution contained in the treatment tank is preferably at least 5 mL.

When the salt tolerance imparting treatment is performed in the cultivation tank, for example, the necessary amount of treatment solution can be suppressed by adjusting the amount of cultivation solution in the cultivation tank so as to be smaller than usually used for the cultivation step (solution amount adjustment step), mixing the salt tolerance imparting agent into the adjusted amount of cultivation solution in the cultivation tank (mixing step), and growing the plant in the cultivation tank for 1 hour or more to thereby contact the tolerance imparting agent with the root of the plant. The adjustment of the amount of cultivation solution can be done by terminating the water supply to the cultivation tank and promoting drainage from the cultivation tank. After the salt tolerance imparting treatment, the treatment solution in the cultivation tank is drained, and subsequently, the cultivation solution is supplied to the cultivation tank to the same level as in the usual cultivation. Then, the cultivation step is resumed by supplying water and draining under normal conditions. When the salt tolerance imparting agent is composed of a material, such as the microorganism, which does not adversely affect the plant even in the event of excessive intake of the material, the cultivation solution may be supplied without draining the treatment solution, and the water supply and drainage may be initiated under the normal water supply and drainage conditions.

The salt tolerance imparting treatment must be carried out before the plant loses the salt tolerance acquired by the previous salt tolerance imparting treatment. The timing or frequency of and the interval between the salt tolerance imparting treatments can be set empirically in consideration of the kind of the plant, the kind of the salt tolerance imparting agent, the sodium chloride concentration of the cultivation solution or the like. For example, by repeating the salt tolerance imparting treatment with a frequency of about once per 1 to 2 months, the plant can be grown stably for a long time even under high salinity environment.

When the salt tolerance imparting agent is a microorganism that imparts the salt tolerance to the plant by adhering to the root thereof, a sufficient amount of microorganism need to adhere to the root in order for the plant to acquire sufficient salt tolerance. Therefore, it is preferable to periodically measure the amount of microorganism adhering to the root of the plant. By monitoring the amount of microorganism adhering to the root, the salt tolerance imparting treatment can be carried out promptly as soon as the amount of microorganism adhering to the root becomes small, before the lowered salt tolerance of the plant actually begins to influence the growth of the plant. The monitoring of the amount of microorganism can be carried out, for example, by allowing a plurality of plants to simultaneously grow under the same condition, and determining the amount of microorganism adhering to the root(s) with respect to at least one plant taken away from a cultivation pot used for growing the plants. The determination of the amount of microorganism can be carried out by a generally employed method such as an agar plate surface smearing method in which a sample obtained by appropriately diluting a microorganism recovered from the root is uniformly smeared on a flat plate medium with a Conradi rod (bacteria spreader) or the like, and the number of colonies formed by culturing the microorganism is counted.

INDUSTRIAL APPLICABILITY

According to the hydroponic method of the present invention, a plant originally having low salt tolerance can be hydroponically grown stably for a long time with a cultivation solution having a sodium chloride concentration of 1% by mass or more.

The invention claimed is:

1. A method for hydroponic plant cultivation under high salinity environment, comprising a cultivation step of hydroponically growing a plant with a cultivation solution having a sodium chloride concentration of 1% by mass or more, during which a salt tolerance imparting treatment is performed more than once by bringing a salt tolerance imparting agent into contact with at least a part of a root of the plant, thereby maintaining salt tolerance of the plant,
wherein:
the salt tolerance imparting agent is at least one selected from the group consisting of a microorganism having a salt resistance imparting effect, a culture supernatant of the microorganism, and a drug having a salt resistance imparting effect; and each repeat of the salt tolerance imparting treatment lasts for one day to seven days, and the salt tolerance imparting treatment is repeated with a frequency of once per 1 to 2 months.

2. The method according to claim 1, wherein the salt tolerance imparting treatment is a treatment of soaking at least a part of the root of the plant into a treatment solution which contains the salt tolerance imparting agent, and has a sodium chloride concentration of 1% by mass or more.

3. The method according to claim 2, wherein at least a part of the root of the plant is held in the treatment solution for 1 hour or more.

4. The method according to claim 2, wherein the treatment solution further comprises magnesium chloride in an amount of 0.5% by mass or less.

5. The method according to claim 1, wherein the salt tolerance imparting agent comprises at least one microorganism.

6. The method according to claim 1, wherein the salt tolerance imparting agent comprises at least one microorganism that imparts the salt tolerance to the plant by adhering to the root, and
the concentration of the microorganism in the treatment solution is $10^3$ CFU/mL or more.

7. The method according to claim 1, which is performed using a hydroponic cultivation apparatus comprising:
a cultivation tank for storing the cultivation solution;
a cultivation pot for accommodating the plant; and
a float having one or more through-holes for fitting the cultivation pot, which is floated on the surface of the cultivation solution.

8. The method according to claim 7, wherein the salt tolerance imparting treatment comprises:
a water level adjustment step of adjusting an amount of water in the cultivation tank to be smaller than that in the cultivation step;
a mixing step of mixing the salt tolerance imparting agent into the cultivation solution in the cultivation tank after the water level adjustment step; and
a treatment step of cultivating the plant for at least one hour after the mixing step, while allowing the root of the plant to be in contact with the salt tolerance imparting agent.

9. The method according to claim 7, wherein the salt tolerance imparting treatment comprises:
a transfer step of allowing the float with the cultivation pot accommodating the plant to float on a surface of the cultivation solution, the cultivation pot being fitted into the through-hole of the float; and
a treatment step of cultivating the plant for at least one hour after the transfer step, while allowing the root of the plant to be in contact with the salt tolerance imparting agent.

* * * * *